US010202550B2

(12) United States Patent
Vindstad et al.

(10) Patent No.: US 10,202,550 B2
(45) Date of Patent: Feb. 12, 2019

(54) PROCESS FOR STABILIZING AN OIL-IN-WATER OR WATER-IN-OIL EMULSION

(71) Applicant: STATOIL PETROLEUM AS, Stavanger (NO)

(72) Inventors: Jens Emil Vindstad, Stavanger (NO); Heidi Mediaas, Stavanger (NO); Knut Vebjørn Grande, Stavanger (NO)

(73) Assignee: Equinor Energy AS, Stavanger (NO)

( * ) Notice: Subject to any disclaimer, the term of this patent is extended or adjusted under 35 U.S.C. 154(b) by 193 days.

(21) Appl. No.: 14/980,600

(22) Filed: Dec. 28, 2015

(65) Prior Publication Data

US 2016/0199803 A1 Jul. 14, 2016

Related U.S. Application Data

(63) Continuation of application No. 12/743,358, filed as application No. PCT/GB2008/003875 on Nov. 17, 2008, now Pat. No. 9,222,035.

(30) Foreign Application Priority Data

Nov. 16, 2007 (GB) .................................. 0722570.9
Nov. 16, 2007 (GB) .................................. 0722591.5

(51) Int. Cl.
| | | |
|---|---|---|
| *B01F 3/08* | (2006.01) | |
| *A23L 33/10* | (2016.01) | |
| *B01F 17/00* | (2006.01) | |
| *C10M 129/56* | (2006.01) | |
| *C10M 129/58* | (2006.01) | |
| *C10G 31/08* | (2006.01) | |
| *C07C 51/347* | (2006.01) | |
| *C07C 51/41* | (2006.01) | |
| *C07C 51/46* | (2006.01) | |
| *C10M 129/93* | (2006.01) | |
| *C10G 19/02* | (2006.01) | |
| *C10G 29/06* | (2006.01) | |

(52) U.S. Cl.
CPC .............. *C10G 31/08* (2013.01); *A23L 33/10* (2016.08); *C07C 51/347* (2013.01); *C07C 51/412* (2013.01); *C07C 51/46* (2013.01); *C10G 19/02* (2013.01); *C10G 29/06* (2013.01); *C10M 129/56* (2013.01); *C10M 129/58* (2013.01); *C10M 129/93* (2013.01); *A23V 2002/00* (2013.01); *B01F 3/0807* (2013.01); *B01F 17/0021* (2013.01)

(58) Field of Classification Search
CPC .... B01F 3/0807; B01F 17/0021; A23L 33/10; A23V 2002/00; C07C 51/412; C07C 51/347; C07C 51/46; C10G 19/02; C10G 29/06; C10G 31/08; C10M 129/56; C10M 129/93; C10M 129/58

USPC .......... 516/109; 508/465; 562/498; 426/271, 426/329, 546, 602, 604

See application file for complete search history.

(56) References Cited

U.S. PATENT DOCUMENTS

| | | | |
|---|---|---|---|
| 2,003,640 A | 6/1935 | Wunsch | |
| 2,227,811 A | 1/1941 | Franz | |
| 2,537,576 A | 1/1951 | Dunlap | |
| 2,769,767 A | 11/1956 | Gifford et al. | |
| 4,555,352 A | 11/1985 | Garner et al. | |
| 6,464,859 B1 | 10/2002 | Duncum et al. | |
| 6,627,069 B2 | 9/2003 | Greaney | |
| 8,084,264 B2 | 12/2011 | Marshall | |
| 8,663,455 B2 | 3/2014 | Levine | |
| 8,674,161 B2* | 3/2014 | Mediaas | C10G 25/003 208/263 |
| 9,222,035 B2* | 12/2015 | Vindstad | C10G 19/02 |
| 2006/0016723 A1 | 1/2006 | Tang et al. | |
| 2007/0267325 A1 | 11/2007 | Vu | |
| 2007/0298505 A1 | 12/2007 | Smith | |
| 2008/0199963 A1 | 8/2008 | Smith et al. | |
| 2010/0147739 A1 | 6/2010 | Levine | |
| 2010/0160680 A1 | 6/2010 | Levine et al. | |
| 2010/0190260 A1 | 7/2010 | Marshall | |
| 2010/0292349 A1* | 11/2010 | Vindstad | C10G 19/02 516/109 |
| 2012/0190907 A1* | 7/2012 | Mediaas | C10G 25/003 585/824 |
| 2012/0283147 A1 | 11/2012 | Vijn | |

(Continued)

FOREIGN PATENT DOCUMENTS

| | | |
|---|---|---|
| CN | 1418934 A | 5/2003 |
| DE | 2144047 A1 | 4/1973 |

(Continued)

OTHER PUBLICATIONS

B. Brocart et al., "ARN-Type Naphthenic Acids in Crudes: Analytical Detection and Physical Properties", Journal of Dispersion Science and Technology, vol. 28, Issue 3, 2007, pp. 331-337, (Published online: Apr. 4, 2007), online @ http://www.tandfonline.come/doi/abs/10.1080/01932690601107161.

(Continued)

*Primary Examiner* — Daniel S Metzmaier

(74) *Attorney, Agent, or Firm* — Knobbe, Martens, Olson & Bear, LLP

(57) ABSTRACT

A process for the preparation of at least one ARN acid or salt thereof comprising: (I) allowing at least one ARN acid salt to form during the production of crude oil in the presence of water; (II) removing at least 5 wt % of the formed at least one ARN acid salt, e.g. from the oil water interface; and optionally (III) converting said salt into an acid.

34 Claims, 1 Drawing Sheet

(56) References Cited

U.S. PATENT DOCUMENTS

2012/0330057 A1    12/2012    Levine et al.
2017/0269042 A1*   9/2017    Paek ..................... G01N 30/96

FOREIGN PATENT DOCUMENTS

| | | |
|---|---|---|
| EP | 1840567 A | 10/2007 |
| EP | 1870706 A1 | 12/2007 |
| GB | 2356404 A | 5/2001 |
| WO | 97/08271 A1 | 3/1997 |
| WO | 97/08275 A1 | 3/1997 |
| WO | 99/43766 A1 | 9/1999 |
| WO | 02/18519 A1 | 3/2002 |
| WO | 2005/100512 A1 | 10/2005 |

OTHER PUBLICATIONS

Baugh, et al., "Characterization of a calcium naphthanate deposit and the ARN acid discovery," 2004, vol. 49, No. 3, 274-276.

Baugh, T.D. et al., "The discovery of high molecular weight naphthenic acids (ARN Acid) responsible for calcium naphthenate deposits", Conference Info: SPE 93011, SPE International Symposium on Oilfield Scale, May 11, 2005, pp. 8-14.

Brandal et al, "Isolation and Characterization of Naphthenic Acids from a Metal Naphthenate Deposit: Molecular Properties at Oil-Water and Air-Water Interfaces", Journal of Dispersion Science and Technology, 27, pp. 295-305 (2006—month unknown).

Database WPI Week 200356 Thomson Scientific, London, GB; AN 2003-588024 XP002544329.

Hawley's Condensed Chemical Dictionary, 2007, John Wiley & Sons Inc., (headword=Naphthenic Acid), Online @ http://onlinelibrary.wiley.com/book/10.1002/9780470114735/titles (Published Online: Mar. 15, 2007), pp. 1 of 1.

Jones, et al., "Determination of naphthenic acids in crude oils using nonaqueous ion exchange solid-phase extraction," Feb. 2001, Anal. Chem., vol. 73, No. 3, 703-707.

Lutnaes, et al., "Archaeal C80 isoprenoid tetraacids responsible for naphthenate deposition in crude oil processing", Org. Biomol. Chem., 2006, vol. 4, pp. 616-620.

Mapolelo, et al., "Chemical specification of calcium and sodium naphthenate deposits by electrospray ionization FT-ICR mass spectrometry," Energy & Fuels, Jan. 2009, vol. 23, No. 1, 349-355.

Simon, et al., "Determination of C80 tetra-acid content in calcium naphthenate deposits," Journal of Chromatorgraphy A, Jun. 2008, vol. 1200, No. 2, 136-143, XP022808375.

Teixeira, et al., "Extraction and fractionation of petroleum naphthenic acids with solid media," Petroleum Chemistry Division Preprints, 2002, vol. 47, No. 1, 1-3.

International Preliminary Report dated May 18, 2010 for International Application No. PCT/GB2008/003875.

International Search Report issued in PCT/GB2008/003875 dated Feb. 1, 2010.

Norwegian Search Report in Norwegian Patent Application No. 20092378, dated Jan. 20, 2010.

* cited by examiner

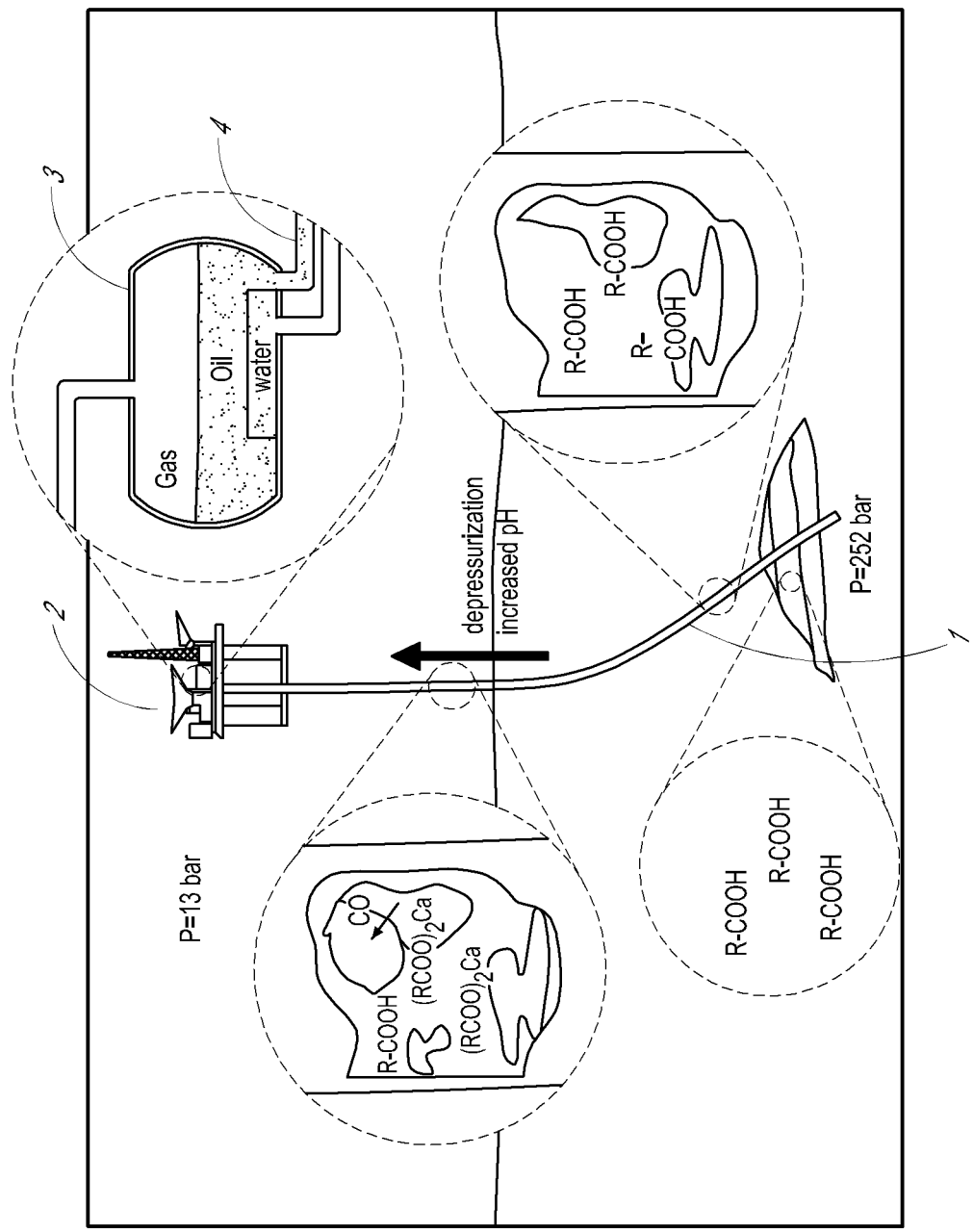

PROCESS FOR STABILIZING AN OIL-IN-WATER OR WATER-IN-OIL EMULSION

INCORPORATION BY REFERENCE TO ANY PRIORITY APPLICATIONS

This application is a Continuation Application of U.S. application Ser. No. 12/743,358, filed Jul. 9, 2010, which is the U.S. National Phase of International Application No. PCT/GB2008/003875, filed Nov. 17, 2008, designating the U.S. and published in English as WO 2009/063230 on May 22, 2009 which claims the benefit of Great Britain Patent Application Nos. 0722591.5 and 0722570.9, all of which were filed on Nov. 16, 2007. Any and all applications for which a foreign or domestic priority claim is identified in the Application Data Sheet as filed with the present application are hereby incorporated by reference under 37 CFR 1.57.

FIELD OF THE INVENTION

This invention relates to a process for the isolation of ARN acids or derivatives thereof as well as to applications of ARN acids or derivatives thereof and manipulation thereof into a form suitable for those applications.

The amount of acidic crude oil produced around the globe is increasing as more sources of oil are found. Acidic crude oils contain significant amounts of carboxylic acids and are characterised as high-TAN crudes (total acid number). In the early phase of production, most wells produce oils with low water contents, typically below 0.5 wt %. As time goes by, water break-through occurs giving rise to significantly higher water cuts. This means that the carboxylic acids present in high TAN crudes will be in intimate contact with water during production.

These high TAN oils introduce problems throughout the hydrocarbon value chain due to their high content of carboxylic acids. Of greatest concern are the formation of naphthenate deposits which occur when the crude oil is brought to the surface in the presence of water. These deposits can block all manner of equipment which can lead to process irregularities and potentially production shutdown.

Calcium naphthenate deposition is among the most challenging obstacles to high production regularity in oil fields where acidic crudes are produced. Until a few years ago, it was believed that the naphthenate deposits formed during crude oil production were made up of calcium soaps of naphthenic acids in the crude oil with a slight over-representation of lighter acids. More recent research has shown this to be incorrect.

The real dominating materials are the salts of the so called "ARN" acids, a family of 4-protic carboxylic acids containing 4 to 8 rings in the hydrocarbon skeleton with molecular weights in the range 1227 to 1235 g/mol. The most prominent among these acids exhibits 6 sites of unsaturation (5-member rings) and a molecular weight of 1231; its chemical formula being $C_{80}H_{142}O_8$. The other members of the ARN family either have different numbers of rings and/or additional $CH_2$-groups in the hydrocarbon skeleton. This discovery was reported in Prepr. Pap-Am Chem Soc Div Pet Chem 2004, 49(3), 274 and SPE 93011, SPE 5th Int. Oilfield scale symposium Aberdeen 2005 and has had some fundamental effects on the way in which high TAN crudes are treated. ARN is not an abbreviation but is simply the term which has been coined to define the acids in question.

The mechanism by which the ARN acid salts form is not fully understood but it is envisaged that the calcium salts form as the crude oil is produced from the oil well. It is believed that at the pressures and pH present in the oil reservoir, the calcium salt normally does not form. Moreover, the salt is not formed during production if no water is coproduced because there are essentially no metal ions to form the ARN acid salts. Where the crude is coproduced with water however, e.g. in a field where water breakthrough has occurred, as the material comes to the surface pressure reduces and pH increases due to carbon dioxide release. Under higher pH conditions, calcium ions from water (or any other suitable metal ion) can react with the ARN carboxylic acids naturally present in the crude oil to form calcium salts of the ARN acids, i.e. naphthenates. It is envisaged that this reaction takes place when a pH of around 5-5,5 is reached.

The ARN salt reaction product is essentially insoluble in both oil and water and hence precipitates out in whatever vessel the crude oil is produced into, typically a separator for removing water. The ARN salts accumulate at the oil and water interface and the presence of this material is a major problem for the oil producer. It is a highly viscous semi solid material that can block filters, nozzles, instrument outtakes, pumps and pipes in oilfield machinery. The industry therefore takes steps to suppress the formation of the ARN acid salts, either by pH-regulation or chemical injection.

In some cases, suppression of the ARN salt formation can be achieved by adding a water soluble acid to a well with a high water cut. Acid injection reverses ARN salt formation as increasing pH is a prerequisite for its formation.

This solution is expensive however and may cause long term corrosion of equipment so proprietary ARN acid salt inhibitors are now used to prevent salt formation in high TAN crude oil refining. These inhibitors are constantly refined, e.g. to take account of the changing nature of the crude being extracted, but have proven extremely effective. In the applicant's oil field at Heidrum, their use has prevented any loss of production for over 10 years. The problem therefore of ARN acid salt formation is one which the industry has overcome successfully by preventing them ever coming into existence.

The present inventors have now realised that the ARN acids or derivatives thereof are a valuable commercial resource. Rather than suppressing their formation therefore, the present inventors have found that the conditions of crude oil production can be controlled to encourage the formation of ARN acid salts. Once formed, the salts can then be removed and optionally returned to the acid form for derivatisation or for direct use in a variety of end applications discussed further below. The remaining crude oil can then be treated in the normal way and used to form all manner of petrochemical products. No one before has appreciated that the ARN materials are a valuable resource in their own right so no commercial process for crude oil production actually encourages their formation or actively seeks to remove them and place them in a form suitable for industrial use.

It will be appreciated that ARN acids or salts thereof have previously been extracted from crude oil in very small quantities for characterisation or screening purposes. Oil producers may well remove a small sample of such acids to determine the overall ARN acid content of a crude with a view to working out how best to suppress their formation. A large scale removal of ARN material, as carried out in the process of the current application where at least 5% of that material has never before been disclosed as no-one has before realised that ARN acids and salts are valuable commercial products in their own right.

It has been found that ARN acids have applications as food additives, lubricants, emulsifiers and surfactants. Moreover, being a by-product of crude oil production, the ARN acid salts are readily available and are cheap to produce. Thus, viewed from one aspect the invention provides a process for the preparation of at least one ARN acid or salt thereof comprising:

(I) allowing at least one ARN acid salt to form during the production of crude oil in the presence of water;

(II) removing at least 5 wt % of the formed at least one ARN acid salt, e.g. directly from the oil water interface; and optionally (III) converting said salt into an acid.

In a preferred embodiment the invention provides a process for the preparation of at least one ARN acid comprising:

(I) allowing at least one ARN acid salt to form during the production of crude oil in the presence of water;

(II) removing at least 5 wt % of the formed at least one ARN acid salt;

(III) if necessary, removing water or oil from the ARN acid salt, e.g. by azeotropic distillation or by an organic washing procedure;

(IV) acidifying said ARN acid salt to form an ARN acid;

(V) optionally cleaning said ARN acid, e.g. by passing it through an ion exchange column.

As discussed in detail below, whilst ARN acid salts tend to form spontaneously in oil isolated from fields where there is water breakthrough (as water and oil are produced from the well together), it is also within the scope of the invention to isolate an ARN acid or salt thereof from oil derived from a field or a production well where water breakthrough has not occurred. The ARN acid is still present in such an oil but the salt of it does not form on oil production as there is no cation present to form the salt. The inventors have realised that if such a counterion is provided, an ARN acid salt can form from essentially any crude oil. Moreover, this process can be effected in any vessel meaning the skilled man can dedicate a vessel to the formation of an ARN acid or salt thereof and can tailor the amount of ARN acid salt he makes to meet demand. Moreover, this process has the advantage that the nature of the metal ion used to form the salt of the ARN acid can be varied and is not dependent on the nature of the cations in the water in the oil field where typically calcium ions dominate.

Thus, viewed from another aspect the invention provides a process for the preparation of an ARN acid or salt thereof comprising (I) adding at least one metal ion to a crude oil at a pH sufficiently high to form an ARN acid salt, e.g. a pH of at least 5;

(II) separating at least a part of the formed ARN acid salt from the crude oil; and optionally (III) converting said salt into an acid.

Of course, this process could also be used on a crude oil which had been isolated from a field were water breakthrough had occurred but were the formation of ARN acid salts had been inhibited, e.g. either chemically or by pH manipulation for example.

Viewed from another aspect the invention provides a food additive, lubricant, emulsifier or surfactant comprising an ARN acid or salt thereof.

By ARN acid is meant a polycarboxylic acid with a molecular weight of 1200 to 1300 containing carbon, oxygen and hydrogen atoms. Preferably, the ARN acid is a tetracarboxylic acid with molecular weights in the range 1227 to 1235. Carboxylic acid groups are preferably terminal. Preferably the ARN acids have 4 to 8 rings in the hydrocarbon skeleton. These rings are preferably pentyl rings.

ARN acids preferably contain one or more units of formula A, B or C

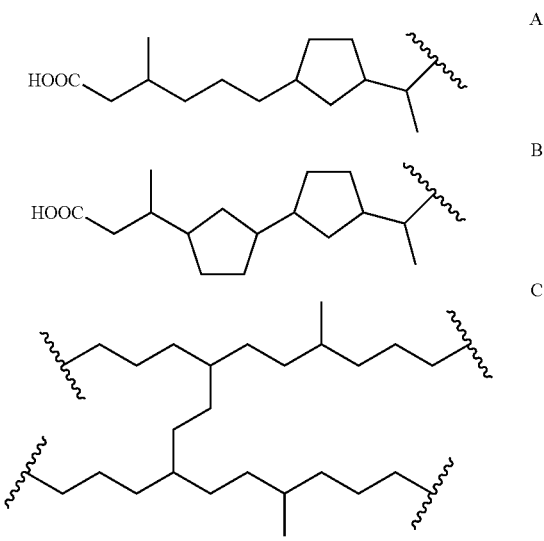

Preferably, the ARN acids of the invention contain all three units A, B and C.

ARN acids are thus a family of very similar materials. The main individual acids may have the molecular formula $C_{80}H_{138}O_8$, $C_{80}H_{140}O_8$, $C_{80}H_{142}O_8$, $C_{80}H_{144}O_8$, $C_{80}H_{146}O_8$, or $C_{81}H_{130}O_8$. Other members of the ARN family are a homologous series based on the addition of $CH_2$ groups to the basic structure, i.e. whose molecular weight is therefore basic structure+n*14 (n=number of additional $CH_2$ groups in the hydrocarbon skeleton).

One ARN acid is depicted below:

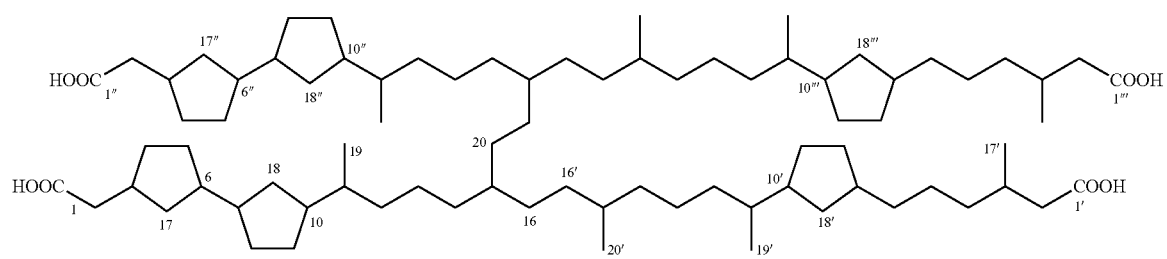 [SMILES: CC(CCCC(C)C1CCC(CCCC(C)CC(=O)O)C1)CCC(CCCC(C)C1CCC(C2CCC(CC(=O)O)C2)C1)CCC(CCCC(C)C1CCC(C2CCC(CC(=O)O)C2)C1)CCC(C)CCCC(C)C1CCC(CCCC(C)CC(=O)O)C1]

It will be appreciated that the process of the invention generally gives rise to a mixture of ARN acids or salts thereof. Whilst a specific ARN acid can be produced by the process of the invention and employed in the various applications suggested herein, it will be appreciated that what is isolated from the crude oil is typically a mixture of ARN acid salts and there is no need to separate this into its constituent compounds. It is preferred therefore if the ARN acid salts are isolated as a mixture.

The ARN acid salts are formed when crude oil containing the ARN acid reacts with cations, e.g. cations present in water, at an appropriate pH and pressure. Water is present during the typical production of crude oil in a field where water breakthrough has occurred and therefore provides a source of cations. Thus, the phrase "during the production of crude oil in the presence of water" means that the crude oil in question is produced in the presence of water because water is present in the oil well and is removed from the well at the same time as the oil. In this embodiment of the invention therefore, it is not necessary to add water to oil or to add metal ions to the oil, rather these are inherently present in the water during the oil production process.

Where the ARN acid salt is being formed from a crude oil derived from a field without water breakthrough or derived from a crude oil where ARN acid salt formation was inhibited during production, it may, of course, be necessary to add to the oil at least one metal ion to form the ARN acid salt. Suitable metal ions include alkaline earth metal ions and transition metal ions, especially barium, strontium, calcium and iron ions. Calcium ions are preferred.

These can be conveniently introduced into the oil in an aqueous solution. The amount of metal ions required is not critical but generally there will be a molar excess of metal ion to ARN acid. Preferably there will a considerable excess of metal ion, e.g. at least 10× molar excess, especially at least 100× molar excess. The amount of ARN acid in a crude oil might vary but typical amounts are of the order of less than 100 parts per million in the crude so the skilled man can determine how much metal ion he needs to add to ensure that there is an excess of metal ion using basic chemical equations. Adding 10% wt of a 1 M cation containing aqueous solution would add a significant excess of metal ions.

To ensure ARN acid salt formation, it is also important to manipulate the pH. Higher pH's tend to encourage the formation of more ARN acid salt. The pH required depends on the nature of the metal salt being formed but for calcium salts ARN acid salts start to form as the pH reaches around 5. The formation of iron salts has been observed to occur at much lower pH's however. Iron salts can start forming at pH's of 2 or more. In general however, the pH should be greater than 5. By increasing this to pH of 7 or more substantially all the ARN acid in a crude can be converted to the salt form. Thus, the pH of the first step of the process of the invention where the ARN acid salt forms should preferably be at least 5, preferably at least 5.5, more preferably at least 6, especially at least 6.5, most especially at least 7. This pH is measured in the water present in the process.

Where ARN acid salt formation was inhibited during production by the addition of acid to minimise pH, it will be appreciated that ARN acid salts are capable of being formed if the pH is increased. Thus, a further process for the manufacture of ARN acid salts is possible if, for example, part of a crude oil/water produced using acid inhibition of ARN acids is simply basified up to a pH of more than 5. It will be appreciated of course that a source of cations must still be present, i.e. some of the water from the field needs to be present to allow the ARN acid salt to form.

Thus, viewed from another aspect the invention provides a process for the preparation of an ARN acid or salt thereof comprising:

(A) adding acid to a crude oil produced from a field where water breakthrough has occurred so as to prevent ARN acid salt formation;

(B) separating a part of the acidified oil/water mixture;

(C) basifying said mixture to a pH of at least 5 to allow the ARN acid salt to form;

(D) removing at least 10% of the formed at least one ARN acid salt; and optionally (E) converting said salt into an acid.

Pressure is also important in allowing formation of the ARN acid salts. At the very high pressures experienced in oil fields, ARN acid salt formation is suppressed but as pressure decreases the salt can form. It is preferred therefore if the ARN acid salts form when the pressure is less than 25 bars, preferably less than 15 bars. Preferably, the reactions take place at ambient pressure.

The ARN acids are preferably isolated from oils with high ARN content, preferably from oils with ARN content greater than 0.1 parts per million, more preferably from oils with ARN content greater than 1 part per million, and most preferably from oils with ARN content greater than 10 parts per million. High ARN content is often found in oils with high TAN (total acid number). Hence, ARN acids are preferably isolated from oils with TAN higher than 0.5, more preferably from oils with TAN higher than 1.0, most preferably from oils with TAN higher than 1.5. However, the ARN acid may also be isolated from oils with very low TAN, provided the oil contains ARN acids.

The crude oils described above are well known in the art and ARN acid formation is currently suppressed in these crudes by the application of known ARN acid inhibitors. In one embodiment present invention, such inhibitors should not be used and the ARN acid salts should be allowed to form naturally during the production process.

As noted above, the salt that forms, typically a calcium salt but feasibly a salt of another metal ion (such as Ba, Fe, Sr), is insoluble in both the oil phase and water phase and therefore precipitates at the interface between these two phases. The new layer which forms consists essentially of the ARN acid salt. This salt may however, to a certain degree, be in a mixture with oil, water and inorganics, dependent on the specific oilfield characteristics. In some cases also asphaltenes, biomass and other impurities might be present in the ARN salt phase.

The ARN acid salt needs to be removed from vessel in which it is formed and this can be achieved readily as it forms at the oil/water interface. The ARN salt can be removed from the interface either continuously or batchwise. ARN salt can also be removed from vessel after draining of oil/water.

At least 5 wt %, preferably at least 10 wt % of the formed ARN acid salt must be removed where the ARN acid salt forms during production from an oil field with water breakthrough although in general at least 5 wt % of the ARN acid salt will be removed irrespective of how it is formed. Preferably at least 25 wt % of the ARN acid salt is removed, more preferably at least 50 wt %, especially at least 75 wt %, more especially at least 90 wt %. Ideally of course, all the ARN acid salt formed is removed, e.g. from the oil water interface.

Determining the amount of ARN acid salt present is a simple matter as the salt exists as a layer between the oil and water phases. Simply be measuring the width of the ARN acid salt layer and knowing the diameter of the vessel in which separation occurs, the amount of ARN acid salt present can be calculated using trivial mathematics (for a cylinder $\pi r^2 h$).

Removal of the ARN acid salt can be achieved by any technique, e.g. by phase separation techniques such as filtration or simply by tapping off the ARN acid salt from the vessel in which the ARN acid salt is present. Removal of the ARN acid salt can also be achieved by draining and gas-freeing the vessel used to isolate and accumulate the ARN acid salt, opening the vessel, and subsequently manually extracting the formed ARN salt deposit. In this case, care should be taken to avoid loss of ARN salt deposit during the draining step. The skilled man can devise all manner of ways of isolating the formed ARN acid salts.

The nature of the vessel in which the ARN acid salts form will change depending on the process in question but conveniently where the process concerns generation of the ARN acid salt through addition of metal ions, the vessel may be a refinery desalter as water is conventionally added to a desalter to remove salt anyway and hence the addition of water to generate the ARN acid salt does not require a major overhaul of the refinery workings as a whole.

Where the ARN salt is formed during production from a well with water breakthrough, the crude material may pass through multiple separators as it is extracted from the production well. In the first separator, most of the oil and gas is separated from the oil before the oil is passed through further separators for further degassing and dewatering. This can take water content from 30% in the first separator down to less than 0.5% by the end of the separation process. The ARN acid salt may form in any of the separators. The amount formed in each separator depends on pressure, temperature, pH, and separation efficiency in the separator.

The ARN acid salts formed can thus be conveniently siphoned off from the separation vessel e.g. via a suitably positioned outlet in the vessel wall. Removing the ARN acid salts can therefore be readily accomplished and can be carried out continuously or batchwise.

It is likely that the ARN acid salts which are removed will be contaminated by water and oil. These can be removed by azeotropic distillation and solvent extraction with hot toluene. Contaminants may also be removed by other means, e.g. simple cleaning using toluene or, other fluid. If the ARN acid salts are isolated without any oil or water present then this step of the process may not be required. Also, if the amount of oil and water present with the ARN acid salts is deemed below a particular threshold (which might vary depending on how pure the ARN acid needs to be), the skilled man may again choose not to carry out this step.

The salt formed at the end of this washing step can then, if desired, be returned to its free acid form. Acidification of the salt, e.g. in a non polar solvent then releases the oil soluble ARN acid itself which partitions into the non polar solvent leaving the metal ion in the aqueous phase. Simple phase separation gives the ARN acid free of metal ion. The acid used can be any known acid typically one of the cheapest such as HCl, nitric acid or sulphuric acid.

If desired, the ARN acid can then be cleaned to ensure that it is in a form suitable for use in the applications below. By cleaning therefore is meant improving purity. It is possible that the ARN acid obtained at this stage of the process may still be associated with some crude oil impurities and these can be removed using various procedures such as chromatography, solid/liquid extraction and liquid/liquid extraction.

Ideally, the acid can be purified further e.g. using ion exchange principles as described in SPE 80404, Aberdeen 2003. The overall principle is that the carboxylic acids in an organic solvent are selectively extracted onto the resin and subsequently recovered by back extraction into a solvent that can easily be removed by evaporation.

The inventors have also realised however, that the quantity of ARN acids formed from an entire oilfield may exceed demand for them. In a field with water breakthrough therefore, it may not be desirable to isolate all the ARN acid salt which the field could yield. Excess ARN acid salt might be more valuable if kept within the oil. They have therefore realised that a smaller amount of ARN acid can be isolated if an amount of crude oil is separated from the majority of the crude oil being removed from the well before addition of the ARN acid salt inhibiting chemicals/acidification. In this way, the major part of the crude may be treated with ARN inhibiting chemicals or acidified and hence manipulated as is known in the art. The remaining part of the crude is not treated with ARN inhibiting chemicals or acidified to encourage formation of ARN acid salts which can then be isolated and treated to form the valuable commercial products of this invention.

Alternatively, a process can be run batchwise where inhibiting chemicals/acidification are used periodically to prevent ARN acid salt formation whilst at other times salt formation is encouraged and isolated using techniques described above.

The invention thus allows the skilled man to isolate ARN acids in high purity in the free acid form. These acids can then be used in end applications discussed in more detail below. However, it is of course possible, if desired, to derivatise those acids into other compounds. Thus, various salts of the ARN acids might be made by conventional salt formation techniques. Calcium salts could be reformed albeit in much greater purity than obtained during the isolation process. One or more of the carboxylic acids present could be converted into an ester using standard ester formation chemistry. The acid functionalities could be reduced to aldehydes or even to methyl groups to form a high molecular weight hydrocarbon. The carboxylic acids could be converted to more active species such as acid chlorides for coupling with nucleophiles. The conversion of carboxylic, acids to amides, nitriles, imides, hydrazones, and so on is well known. J. March, Advance organic chemistry contains countless disclosures of how to convert carboxylic acids to other useful chemical entities and these reactions are generally applicable to the ARN acids.

The invention therefore covers not only ARN acids but derivatives thereof where said derivative is, for instance, a salt or ester.

A further option for the isolation of ARN acids according to the invention involves obtaining them directly from the crude oil itself, without converting them to the insoluble salt. ARN acids can therefore be isolated from crude oil by chromatography, ion exchange or extraction. Of these options, ion exchange is preferred, especially using an acid ion exchange resin such as Sephadex A-25.

Applications

The ARN acid or acids of the invention can be employed in a variety of end uses, all of which form further aspects of the invention. It has been particularly found that ARN acids have applications as food additives, lubricants, emulsifiers or as surfactants. When formulated as food additives it is within the scope of the invention for the carboxyl groups to be functionalised to change the polarity/charge on the molecule. When formulated as lubricants it is within the scope of the invention for the carboxyl groups to be functionalised to change the total base number of the material. Suitable functional groups include esters and amides. The resulting ARN acid derivative may have a higher base number.

The amphiphilic nature of the ARN acid molecules also makes them ideal as surfactants. Again, to maximise their use as a surfactant the skilled man may choose to derivatise the carboxyl groups of the ARN acid.

When present as a food additive, the ARN acid or salt may act, inter alia, as a surfactant, emulsifier, bulking agent, acidity regulator, thickener or preservative and could be added to any food type. The amounts added reflect typical amounts of such materials used in the food industry, e.g. less than 1 wt % of the additive.

Viewed from another aspect therefore the invention provides use of an ARN acid, derivative or salt thereof as a food additive.

Viewed from another aspect therefore the invention provides use of an ARN acid, derivative or salt thereof as a lubricant, emulsifier or surfactant.

Viewed from another aspect there is provided a method of stabilising a oil in water or water in oil emulsion comprising adding to a mixture of oil in water or water in oil an ARN acid, derivative or salt thereof.

Viewed from another aspect the invention provides an emulsion comprising an ARN acid, derivative or salt thereof.

When used as surfactants, the ARN acid might have an application in the food or cosmetics industries, for example.

The invention will now be described further with reference to the following non limiting examples and figures.

BRIEF DESCRIPTION OF THE DRAWING

FIGURE shows isolation of ARN acid salts from a oil field with water breakthrough. Oil and water from the bed are transported up pipe (1) to platform (2) and into separator (3). As no steps are taken to prevent ARN acid salt formation, ARN acid salts form in pipe (1) as the pressure reduces and pH increases through carbon dioxide emission. When the pH of the water reaches 5, the salt begins to form and is thus present in the separator (3) at the interface between the oil and water phases.

The ARN acid salt is tapped of via conduit (4) into a storage vessel (not shown) where it can be washed and acidified to return the salt to its free acid form.

EXAMPLE 1

Isolation of ARN Acid

An ARN acid salt precipitate was removed from the interface between oil and water phases in crude oil production from a well with water breakthrough. Water and oil were removed from the precipitate by azeotropic distillation and solvent extraction using hot toluene followed by methylene chloride. The solvents were removed by vacuum drying at 60° C.

The resulting deposit was refluxed with 2M HCl and toluene for a time long enough to convert the ARN acid salts to ARN acids. The acid partitioned into the toluene and metal ion into the aqueous phase. The solvent was removed to leave a deposit containing ARN acids.

EXAMPLE 2

Cleaning of ARN Acid

QAE Sephadex A-25 resin is provided in deactivated form with the active sites protected with chloride ions. The resin must therefore be activated before use. This is achieved using 1M sodium bicarbonate in sodium carbonate buffer. Typically 75 ml of buffer solution is required per gram of resin. The resin is then treated with deionised water and then methanol before the ARN acids are added dissolved in toluene.

After washing the resin with more toluene, and then a toluene methanol mix 2:1), 1M formic acid, in toluene methanol (1:1) was used to recovered the ARN acids.

What is claimed is:
1. A process for preparing a food comprising:
   (I) allowing at least one ARN acid salt to form during the production of crude oil in the presence of water;
   (II) removing at least 5 wt % of the formed at least one ARN acid salt;
   (III) optionally converting said salt into an acid;
   (IV) optionally functionalizing the carboxyl groups of said ARN acid salt or said acid to change the polarity/charge on the molecule and form an ARN acid derivative; and
   (V) adding said ARN acid salt, said acid or said ARN acid derivative to a food.
2. A process as claimed in claim 1, wherein at least 5 wt % of the formed at least one ARN acid salt is removed from the oil water interface.
3. A process as claimed in claim 1 wherein said salt is a calcium salt.
4. A process as claimed in claim 1 wherein the pH of step (I) is at least 5.
5. A process as claimed in claim 1 wherein the pressure during ARN acid salt formation is ambient.
6. A process as claimed in claim 1 wherein the ARN acid content of the crude oil is at least 10 ppm.
7. A process for preparing a lubricant comprising:
   (I) allowing at least one ARN acid salt to form during the production of crude oil in the presence of water;
   (II) removing at least 5 wt % of the formed at least one ARN acid salt;
   (III) optionally converting said salt into an acid; and
   (IV) functionalizing the carboxyl groups of said ARN acid salt or said acid to form an ester or amide group.
8. A process as claimed in claim 7, wherein at least 5 wt % of the formed at least one ARN acid salt is removed from the oil water interface.
9. A process as claimed in claim 7 wherein said salt is a calcium salt.
10. A process as claimed in claim 7 wherein the pH of step (I) is at least 5.
11. A process as claimed in claim 7 wherein the pressure during ARN acid salt formation is ambient.
12. A process as claimed in claim 7 wherein the ARN acid content of the crude oil is at least 10 ppm.
13. A process for preparing a food comprising:
   (I) allowing at least one ARN acid salt to form during the production of crude oil in the presence of water;
   (II) removing at least 5 wt % of the formed at least one ARN acid salt;
   (III) if necessary, removing water or oil from the ARN acid salt;
   (IV) acidifying said ARN acid salt to form an ARN acid;
   (V) optionally cleaning said ARN acid;
   (VI) optionally functionalizing the carboxyl groups of said ARN acid to change the polarity/charge on the molecule and form an ARN acid derivative; and
   (V) adding said ARN acid or said ARN acid derivative to a food.

14. A process as claimed in claim 13, wherein the water or oil is removed from said ARN acid salt in step (III) by azeotropic distillation.

15. A process as claimed in claim 13, wherein step (V) is carried out by passing said ARN acid through an ion exchange column.

16. A process as claimed in claim 13 wherein said salt is a calcium salt.

17. A process as claimed in claim 13 wherein the pH of step (I) is at least 5.

18. A process as claimed in claim 13 wherein the pressure during ARN acid salt formation is ambient.

19. A process as claimed in claim 13 wherein the ARN acid content of the crude oil is at least 10 ppm.

20. A process for preparing a lubricant comprising:
    (I) allowing at least one ARN acid salt to form during the production of crude oil in the presence of water;
    (II) removing at least 5 wt % of the formed at least one ARN acid salt;
    (III) if necessary, removing water or oil from the ARN acid salt;
    (IV) acidifying said ARN acid salt to form an ARN acid;
    (V) optionally cleaning said ARN acid; and
    (VI) functionalizing the carboxyl groups of said ARN acid to form an ester or amide group.

21. A process as claimed in claim 20, wherein the water or oil is removed from said ARN acid salt in step (III) by azeotropic distillation.

22. A process as claimed in claim 20, wherein step (V) is carried out by passing said ARN acid through an ion exchange column.

23. A process as claimed in claim 20 wherein said salt is a calcium salt.

24. A process as claimed in claim 20 wherein the pH of step (I) is at least 5.

25. A process as claimed in claim 20 wherein the pressure during ARN acid salt formation is ambient.

26. A process as claimed in claim 20 wherein the ARN acid content of the crude oil is at least 10 ppm.

27. A process for preparing a food comprising
    (I) adding at least one metal ion to a crude oil at a pH of at least 5 so as to form an ARN acid salt;
    (II) separating at least a part of the formed ARN acid salt from the crude oil;
    (III) optionally converting said salt into an acid;
    (IV) optionally functionalizing the carboxyl groups of said ARN acid salt or said acid to change the polarity/charge on the molecule and form an ARN acid derivative; and
    (V) adding said ARN acid salt, said acid or said ARN acid derivative to a food.

28. A process as claimed in claim 27 wherein said metal ion is a calcium ion.

29. A process as claimed in claim 27 wherein the pressure during ARN acid salt formation is ambient.

30. A process as claimed in claim 27 wherein the ARN acid content of the crude oil is at least 10 ppm.

31. A process for preparing a lubricant comprising
    (I) adding at least one metal ion to a crude oil at a pH of at least 5 so as to form an ARN acid salt;
    (II) separating at least a part of the formed ARN acid salt from the crude oil;
    (III) optionally converting said salt into an acid; and
    (IV) functionalizing the carboxyl groups of said ARN acid salt or said acid to form an ester or amide group.

32. A process as claimed in claim 31 wherein said metal ion is a calcium ion.

33. A process as claimed in claim 31 wherein the pressure during ARN acid salt formation is ambient.

34. A process as claimed in claim 31 wherein the ARN acid content of the crude oil is at least 10 ppm.

* * * * *